United States Patent [19]

Capurro

[11] 4,352,357
[45] Oct. 5, 1982

[54] TIMED DIATHERMOCAUTERY COMPRISING A TIMER UNAFFECTED BY DISTURBANCES OF ELECTROMAGNETIC ORIGIN

[76] Inventor: Sergio Capurro, Via Rimassa, 51, Genoa, Italy

[21] Appl. No.: 112,788

[22] Filed: Jan. 16, 1980

[30] Foreign Application Priority Data

Jan. 23, 1979 [IT] Italy .............................. 12432 A/79

[51] Int. Cl.³ .......................................... A61B 17/39
[52] U.S. Cl. ........................... 128/303.13; 128/303.18
[58] Field of Search ...................... 128/303.13, 303.14, 128/303.17, 303.18

[56] References Cited

U.S. PATENT DOCUMENTS

| 3,315,678 | 4/1967 | Donelson | 128/303.18 |
| 3,359,982 | 12/1967 | Guiorguiev | 128/303.18 |
| 4,074,719 | 2/1978 | Semm | 128/303.17 X |
| 4,167,187 | 9/1979 | Biagi | 128/303.13 |
| 4,224,944 | 9/1980 | Roberts | 128/303.18 |

FOREIGN PATENT DOCUMENTS 2821498 11/1978 Fed. Rep. of Germany ....................... 128/303.13

OTHER PUBLICATIONS

Sabah, "A high-frequency coagulator . . . ", EEG & Clin. Nevro., vol. 36, p. 311-313, Mar. 1974.

Primary Examiner—Lee S. Cohen
Attorney, Agent, or Firm—Fidelman, Wolffe & Waldron

[57] ABSTRACT

Timed diathermocautery comprising the combination of a conventional diathermocautery and a timer sufficiently precise for short duration interventions, free of electromagnetic disturbances, wherein the timing capacitor is charged directly because of a drive switch with limitation of the charge duration, in said timer all of the electronic circuits being operated at higher current levels.

6 Claims, 3 Drawing Figures

TIMED DIATHERMOCAUTERY COMPRISING A TIMER UNAFFECTED BY DISTURBANCES OF ELECTROMAGNETIC ORIGIN

This invention is concerned with a timed diathermocautery, the basic feature of which is the capability of accurately proportioning in advance the duration of a discharge and wherein the timer is free of or unaffected by disturbances of electromagnetic nature or origin.

Diathermocauteries are devices generating localized small electrical discharges of high frequency, and are commonly used in numerous applications in surgical and dermatological fields. However, such devices have to be especially set as to discharge duration by completely empirical manual or pedal-operated systems. One of the dermatological fields in which such a diathermocautery is most frequently used is hair-removal or depilation, which is accomplished by introducing the diathermic needle in each piliferous follicle, and the discharge duration is set by a pedal drive controlled by the operator without any automation at all. As a result, it is impossible under such a condition to use consistently repeatable, extremely short, time durations (of the order of 1/10 sec); and, accordingly there is a total lack of treatment uniformity from one to another hair. Therefore, it is necessary to use a rather long lasting low intensity discharge, which may also give rise to some inadequate operation.

On the other hand, a long duration of discharge, which may amount to two seconds, due to heat dispersion, causes a lesion or injury in the tissues adjacent the piliferous bulb, is more painful and gives rise to the possibility of leaving permanent scars due to misadjusted discharge or anomalous movements that the operator's hand might give to the needle.

This quite unnecessary peribulbar textural pain additionally requires a substantial period of time for a complete recovery.

Since the application of a diathermic current is painful, a patient would be intolerant to many applications during each session. Finally, because of a setting exclusively based on the individual operator's sensitiveness and ability, it is most likely that some mistake may occur in the large amount of operations which are required in this type of treatment.

Similar shortcomings are found when using known diathermocauteries for the removal of teleangiectasiae and capillary vessels according to conventional techniques, so that some or a series of closely spaced spotlike scalds are performed, as effected on the capillary course and branches thereof, with the purpose of limiting to the greatest extent the duration of each operation.

Standard diathermocauteries are also used for intraoperating coagulation of vessels and bipolar coagulation, in which such above mentioned disadvantages are found: the considerable time duration of applications with a resulting larger textural damage, a pain proportional to the discharge duration in dermatological applications, possibility of mistakes, possible ineffectiveness of some discharges, and disuniformity of operation.

By using a timed diathermocautery according to the present invention, all of the above mentioned shortcomings are overcome.

Thus, a means is provided for presetting the discharge duration, which for a given set of operations is maintained quite equal and constant for which the individual operations can be programmed in extremely short times, on the order of 1/10 second, or less.

Accordingly, a voltage can be used which is definitely higher than that commonly used, with the advantage of being surely necrotic, and therefore certainly effective for the intended scope.

By using the automatic timing according to the present invention, as a result of the extreme shortness of the discharge, minimal textural lesions are found about the application location. Additionally, the device of the instant invention is less painful to the patient due to the very short discharge duration and to the destruction of the pain perceptive fibers. Therefore, many more operations can be effected in each session so that a lesser number of sessions is needed; and, due to the higher voltages used, a higher degree of certainty in the results is attained to avoid the likelihood of mistakes from the operator. Thus, as the case may be, the operator will preset, time by time, both the duration and intensity of discharges, which will remain constant for all the desired time. Obviously, in particular cases it would also be possible to program long durations of discharges effected by low voltage, while using known techniques as to regularity and automatism.

Particularly, as to removal of capillary vessels, including telangiectasiae, a device according to the present invention allows to operate with extreme easiness and rapidity making the many small required burns which are all the same and with the above mentioned features.

In order to achieve said results, it was above all taken into account the possibility of simply applying a conventional type of electronic timer to a conventional diathermocautery. But this proved to be unfeasible, due to interferences being generated, since the radiofrequency discharge of the diathermocautery produced interfering pulses on such a timer, altering the operating modalities thereof.

Therefore, it was necessary to design a timer free of disturbances of electromagnetic origin or nature, and of which by only way of example an embodiment is described, wherein the following expedients have been adopted to overcome the shortcomings found in conventional timers.

(1) The timing capacitor, normally charged, is discharged to initiate timing directly through the (pedal) drive switch, rather than through an electronic device (such as a transistor) which could easily produce unwanted discharges in the presence of disturbances.

(2) The entire circuit is designed for currents much higher than those usually used, so as to reduce the relative weight of the disturbances.

(3) At critical locations capacitors have been introduced for the purpose of further reducing the disturbance amplitude.

Moreover, for carrying into practice said principle from operating standpoint, since actual timing starts from the moment at which the capacitor discharging circuit is switched off, thus adding thereto in advance the entire period in which such a circuit is closed or connected, to avoid that such an added period should display an undue influence, a discharge duration limiting circuit was introduced in series with said discharging circuit, so that even extended operations of the drive pedal would anyhow provide discharges of short duration.

A timer according to the present invention, the disclosure of which is herein given by only way of example, was provided on the following considerations.

The only type of control for high frequency generating systems of the type considered for a first experimentation (the most critical from the point of view of electromagnetic disturbances, that is spark gap control with a step-up transformer at high frequency) is the switching on and off of the supply voltage (220 V a.c.).

Therefore, an adjustable timer was required (experimentally, the most suitable times are in the range of 0.05 to 1 sec) capable of controlling the supply of a diathermocautery, that is 220 V. with currents in the order of 1 A, with inductive load (such as that just presented by such devices).

The load inductivity and above all the requirement of setting short time intervals along with sufficient repeatability, in addition to reliability considerations, make it unadvisable to use a relay as an actuator; instead, a triac was chosen.

Such a solution has an indetermination of a half-period between the two limit cases, at which the timing terminates just before passing current zero (in which case, switching off is immediate), or just after (in which case, switching off is delayed by a half-period, that is 1/100 sec at 50 Hz).

In the worst of cases, that is of a minimum time of 1/20 sec, this would correspond to an error in the range of $-0+20\%$, that is to say an error of $\pm 10\%$ with respect to the average duration. Such an error, which however does not build up any disturbances, can be eliminated through said triac control, by starting the triac conduction (and timing) at the beginning of a half-period by a timing method based on the count of the half-periods or on the synchronization of timing end with a determined point of the half-period (other than zero passing).

Owing to extremely high intensity of electromagnetic disturbances generated by the diathermocautery, it is impossible to use conventional type of timers, containing bistable elements being energized also by extremely short drive pulses, just as those typically due to disturbances, which may cause undesired startings of timing, or quite prevent the end thereof.

Accordingly, a different principle was adopted: a timing capacitor is discharged by the drive contact and recharged through an adjustable resistance determining the timing duration; the charge level is compared with a predetermined fixed level; at the time of overcoming or out-weighing, timing is ceased.

Practically, comparison is accomplished by connecting the capacitor to the base of a transistor, the emitter of which is connected to a divider (the use of a divider connected to the same voltage charging the capacitor would tend to compensate for the effect of possible variations in the supply voltage on the timing duration). Due to the finite gain of the system, and due to the relative slowness by which the capacitor voltage varies, particularly for longer times, also the current of the comparator transistor collector does not show a step, but a ramp transition; this could generate a disturbance should such a current be directly used as a control on the triac gate electrode, which while admitting an always positive energization both for positive and negative voltages between the two anodes (anode 1 and anode 2), has a different firing sensitiveness in the two cases; accordingly during the descending ramp of the current, gate current values would be passed through as sufficient to cause conduction only during one half-period, and not during the other half-period; which, owing to the prevailingly inductive nature of the load, would readily lead to destructive current values for the triac, and in case for the diathermocautery.

Accordingly, a bistable element was introduced between the comparator and triac, such a bistable element comprising two complementary transistors connected to form a programmable unijunction, by which they could be replaced, if desired.

The lack of sensitivity to disturbances of such a bistable element is assured by the two following factors:

(a) The bistable element has no influence on timing, but exclusively serves for making steep the current trailing edge; and (b) The bistable element is driven on supply, so that it cannot absolutely become improperly energized (being unsupplied rather than simple de-energized).

The adopted timing method, consisting of discharging the timing capacitor directly by the drive contact, would lead to a shortcoming where directly employed, since the capacitor would start to charge only after contact opening; therefore, the triac and load as well would be operated throughout the closure duration of the drive contact, plus the timing duration.

Since the drive contact is usually pedal-operated, the closure time is often not negligible (usually larger than the timing duration). In order to solve such a shortcoming, a current duration limiter was placed in series between said drive contact and timing capacitor, such a limiter switching the circuit off after few milliseconds, as sufficient for discharging the timing capacitor. The circuit is restored to initial conditions only after release of drive contact for at least some tens of milliseconds; then, even if the contact is maintained at closed condition, it is impossible that momentary openings due to dirt or contact defects, or vibrations would cause undesired startings.

An alternate system to such a circuit could consist of an inhibiting circuit, located downstream of the comparator, controlled by the drive contact; in such a case, timing would begin at the opening instead that at the closing of the contact.

The timing system consisting of discharging a normally charged capacitor leads to a shortcoming; at the time of closing of the main supply switch, the capacitor which was obviously discharged, would cause an undesired timing.

A system for overcoming such a shortcoming could consist of charging a normally discharged capacitor. Such a possibility was discarded a priori, as it would cause a temporary overload in the feeder, with deleterious consequences to time repeatability, since the supply would cease to be stable.

Accordingly, an auxiliary circuit was adopted in the feeder or power supply, which upon power supply turn-on limits the voltage step-up rate.

For the operator's convenience, the supply step-up period (during which time repeatability is not assured) is signalled by a warning lamp (LED).

A further warning lamp signals the ignition state, whereas a third warning lamp lights up for the entire timing duration.

In order to retain flexibility to the system, the main energizing switch has 3 positions: (1) timer, (2) disconnected, (3) direct. At the third position, the closure of the energizing contact controls the triac gate. Such an arrangement, similar as to effect and use to the direct control of the diathermocautery through the contact is advantageous for the life of the contact, subjected to minor currents and voltages, and for use safety, since with said main energizing switch at disconnected position, causal operations are impossible even by accidental operation or depression of the pedal.

For a best illustration of the invention, the following drawings are appended by mere way of illustration. In the drawings.

Figure 1:
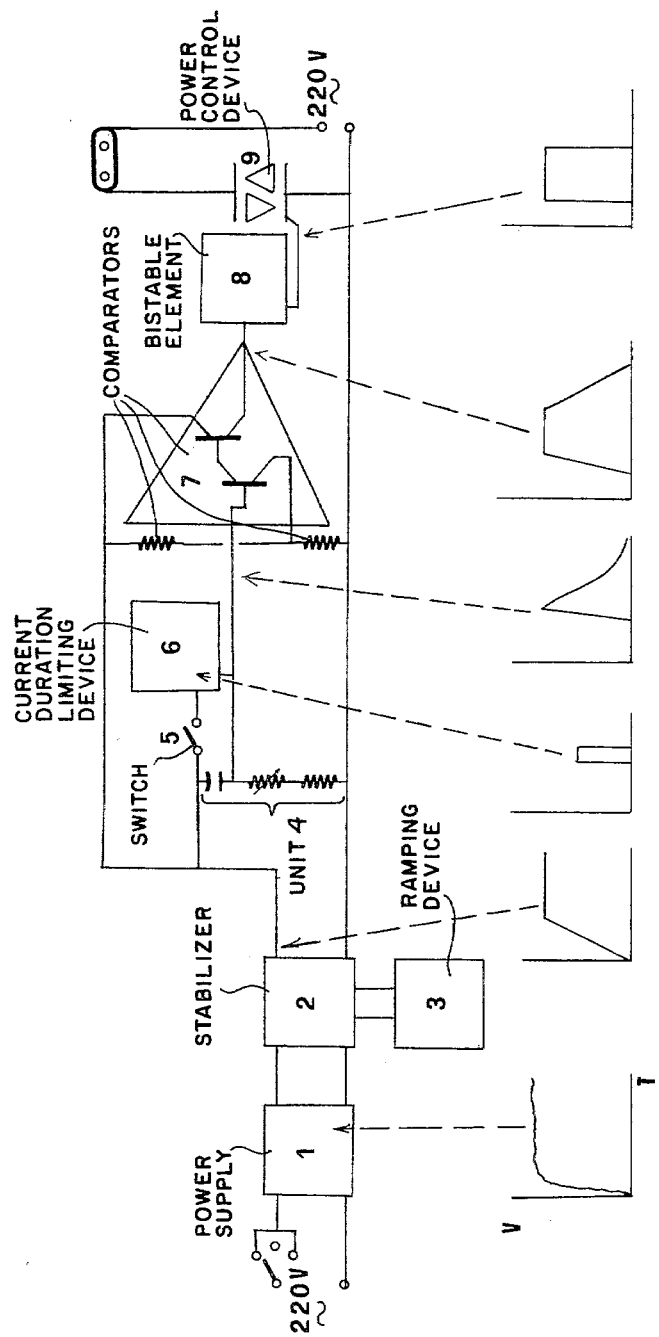
FIG. 1 is a block diagram of a timer according to this invention.

Referring to FIG. 1, a timer comprises a stabilized feeder (power) unit including a feeder (power supply) 1 which provides for transformation from mains 220 V a.c. to about 9 V d.c. which is stabilized to 6 V. by stabilizer 2, fitted with d.c. output voltage ramping device 3. A R-C unit 4, wherein R is variable, generates a ramp of varying duration which is started by switch 5, the action of which is time limited by a current duration limiting device 6; comparator 7 serves the purpose of timing determination by comparing the instantaneous value of the ramp with a fixed voltage and through a bistable element 8 controls the diathermocautery supply drive triac 9.

Figure 2:
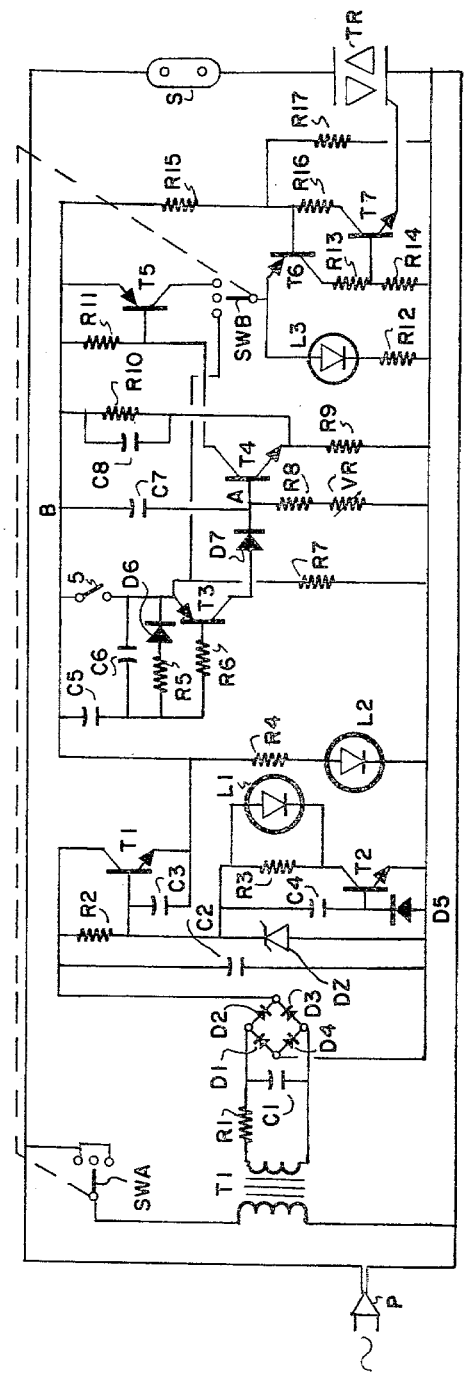
FIG. 2 is a complete electrical diagram for the embodiment of FIG. 1.

An exemplary embodiment of the complete and detailed circuit along with the various connected components can be seen in FIG. 2.

Figure 3:
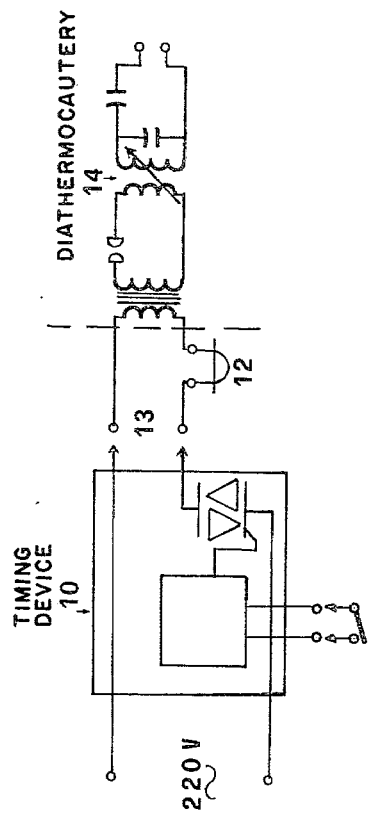
FIG. 3 shows a timed diathermocautery provided by combining the timer of FIG. 1 with a conventional diathermocautery.

In FIG. 3 the method is defined for inserting the timing device 10 in a.c. supply of a diathermocautery. With short circuit plug 12 bridging the original drive contact of a conventional diathermocautery, timing device 10 is connected between A.C. supply and A.C. supply connections 13. Switch 5 is connected to timing device 10 by suitable connector 11.

At the right of the dashed line on the drawing, there is schematically shown the section of conventional diathermocautery 14 which remains unaltered.

Advantageously, a timer comprising blocks 4, 5, 6 and 7 could be used for applications other than those above mentioned in ambients or conditions where a high level of electromagnetic disturbances is present.

I claim:

1. The combination of a timing device and a diathermocautery apparatus for use on a patient and including a power supply in which power is selectively supplied to a load from said power supply, said apparatus having a switch movable between an operate position and a non-operate position, said timing device being immune to electromagnetic disturbances and comprising:
   comparator means for establishing threshold levels of a timing voltage above which said power is supplied to said load;
   timer means for supplying said timing voltage to said comparator means, said timer means comprising a series connected capacitance and resistance in parallel across said power supply; and
   current duration limiting means for activating said timer means when said switch is moved to said operate position and for limiting the amount of time that said timing voltage is supplied to said comparator means when said switch is in said operate position and for providing a set time before which said timer means may be reactivated;
   whereby said timer means may not be accidentally reactivated prior to said set time because of dirty or faulty switch contacts or because of vibrations, and whereby electromagnetic disturbances may not affect the timing device as in electronic timing devices of the integrated circuit type.

2. A combination as in claim 1, wherein said timer means further comprises adjustable resistance means for adjusting and varying the time during which power is supplied to said load.

3. A combination as in claim 1, and further comprising:
   a bistable means and triac power control means for supplying said power to said load from said comparator means;
   whereby damage to said triac power control means is prevented by said bistable means.

4. A combination as in claim 1, and further comprising:
   means for providing a stabilized ramp output from said power supply to said timing device.

5. A combination as in claim 4, and further comprising:
   means for indicating to the operator, respectively, when the power supply is on, when the output from the power supply is rising, and when the timing voltage is above the threshold levels.

6. A combination as in claim 1, wherein, upon movement of said switch to said operate position, a current for activating said timer means via said current duration limiting means is passable only through said switch.

* * * * *